(12) United States Patent
Drmanovic

(10) Patent No.: US 10,195,110 B2
(45) Date of Patent: Feb. 5, 2019

(54) CAPPING DEVICE FOR DISINFECTING MEDICAL CONTAINER

(71) Applicant: Zoran Drmanovic, Palm City, FL (US)

(72) Inventor: Zoran Drmanovic, Palm City, FL (US)

(73) Assignee: DRMA GROUP INTERNATIONAL LLC, Palm City, FL (US)

( * ) Notice: Subject to any disclaimer, the term of this patent is extended or adjusted under 35 U.S.C. 154(b) by 324 days.

(21) Appl. No.: 15/259,211

(22) Filed: Sep. 8, 2016

(65) Prior Publication Data

US 2018/0064604 A1 Mar. 8, 2018

(51) Int. Cl.
| | |
|---|---|
| *A61J 1/14* | (2006.01) |
| *A61L 2/18* | (2006.01) |
| *B65D 51/28* | (2006.01) |
| *B65D 43/16* | (2006.01) |
| *B65D 53/02* | (2006.01) |

(52) U.S. Cl.
CPC ........... *A61J 1/1412* (2013.01); *A61J 1/1406* (2013.01); *A61L 2/18* (2013.01); *B65D 43/16* (2013.01); *B65D 51/28* (2013.01); *B65D 53/02* (2013.01); *A61L 2202/121* (2013.01); *A61L 2202/23* (2013.01)

(58) Field of Classification Search
CPC . A61J 1/1406; A61J 1/1412; A61L 2202/121; A61L 2202/23; A61L 2/18; B65D 43/16; B65D 51/28; B65D 53/02
See application file for complete search history.

(56) References Cited

U.S. PATENT DOCUMENTS

| | | | |
|---|---|---|---|
| 2,400,722 | A | 5/1946 | Swan |
| 4,340,052 | A | 7/1982 | Dennehey et al. |
| 4,440,207 | A | 4/1984 | Genatempo et al. |
| 5,053,003 | A | 10/1991 | Dadson et al. |
| 5,242,425 | A | 9/1993 | White et al. |
| 5,295,975 | A | 3/1994 | Lockwood, Jr. |
| 5,324,264 | A | 6/1994 | Whitaker |
| 5,429,612 | A | 7/1995 | Berthier |
| 5,681,283 | A | 10/1997 | Brownfield |
| 5,792,120 | A | 8/1998 | Menyhay |

(Continued)

FOREIGN PATENT DOCUMENTS

| | | |
|---|---|---|
| EP | 0409180 A1 | 1/1991 |
| EP | 0520930 A1 | 12/1992 |

(Continued)

*Primary Examiner* — Kai Weng
(74) *Attorney, Agent, or Firm* — Cantor Colburn LLP

(57) ABSTRACT

A capping device for disinfection of a medical container is provided. The capping device includes a top portion having an inner surface, a bottom portion having an inner surface and an opening, and a connector. The connector couples the top portion of the capping device to the bottom portion thereof in a manner which permits movement of the top portion between a fully-seated position on the bottom portion of the capping device to form a hollow defined by the inner surface of the top portion of the capping device and the inner surface of the bottom portion thereof, and a position apart from the opening to permit ingress to the vial. The capping device further includes a disinfecting absorbent material disposed inside the hollow and extending through the opening in the inner surface of the bottom portion.

20 Claims, 8 Drawing Sheets

(56) References Cited

U.S. PATENT DOCUMENTS

| | | |
|---|---|---|
| 5,885,249 A | 3/1999 | Irisawa |
| 6,045,539 A | 4/2000 | Menyhay |
| 6,171,287 B1 | 1/2001 | Lynn et al. |
| 6,322,540 B1 | 11/2001 | Grabis et al. |
| 6,391,003 B1 | 5/2002 | Lesch, Jr. |
| 6,409,706 B1 | 6/2002 | Loy |
| 6,547,764 B2 | 4/2003 | Larsen et al. |
| 6,582,408 B1 | 6/2003 | Buch-Rasmussen et al. |
| 6,908,460 B2 | 6/2005 | Distefano |
| 7,682,561 B2 | 3/2010 | Davis et al. |
| 7,815,611 B2 | 10/2010 | Giambattista et al. |
| 7,931,877 B2 | 4/2011 | Steffens et al. |
| 8,065,773 B2 | 11/2011 | Vaillancourt et al. |
| 8,069,523 B2 | 12/2011 | Vaillancourt et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,298,196 B1 | 10/2012 | Mansour |
| 8,328,767 B2 | 12/2012 | Solomon et al. |
| 8,336,151 B2 | 12/2012 | Kerr et al. |
| 8,336,152 B2 | 12/2012 | Vaillancourt et al. |
| 8,343,112 B2 | 1/2013 | Solomon et al. |
| 8,491,546 B2 | 7/2013 | Hoang et al. |
| 8,523,830 B2 | 9/2013 | Solomon et al. |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Vaillancourt et al. |
| 8,696,820 B2 | 4/2014 | Vaillancourt et al. |
| 8,734,384 B2 | 5/2014 | Boyd et al. |
| 8,740,864 B2 | 6/2014 | Hoang et al. |
| 8,784,388 B2 | 7/2014 | Charles et al. |
| 8,961,475 B2 | 2/2015 | Solomon et al. |
| 8,999,073 B2 | 4/2015 | Rogers et al. |
| 9,039,989 B2 | 5/2015 | Liu et al. |
| 9,079,692 B2 | 7/2015 | Solomon et al. |
| 9,114,915 B2 | 8/2015 | Solomon et al. |
| 9,186,707 B2 | 11/2015 | Vaillancourt et al. |
| 9,192,449 B2 | 11/2015 | Kerr et al. |
| 9,259,284 B2 | 2/2016 | Rogers et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 2008/0177250 A1 | 7/2008 | Howlett et al. |
| 2009/0137969 A1 | 5/2009 | Colantonio et al. |
| 2009/0307449 A1 | 12/2009 | Prahlad et al. |
| 2010/0200017 A1* | 8/2010 | Kerr ............. A61B 1/122 134/6 |
| 2010/0272379 A1 | 10/2010 | Hu et al. |
| 2011/0054440 A1 | 3/2011 | Lewis |
| 2012/0302970 A1 | 11/2012 | Tennican |
| 2013/0171030 A1 | 7/2013 | Ferlic et al. |
| 2015/0360021 A1 | 12/2015 | Limdico et al. |
| 2017/0232121 A1 | 8/2017 | Chiu et al. |
| 2018/0085568 A1 | 3/2018 | Drmanovic |

FOREIGN PATENT DOCUMENTS

| | | |
|---|---|---|
| EP | 0832661 A2 | 4/1998 |
| EP | 1336419 A1 | 8/2003 |
| WO | 2015120336 A1 | 8/2015 |

\* cited by examiner

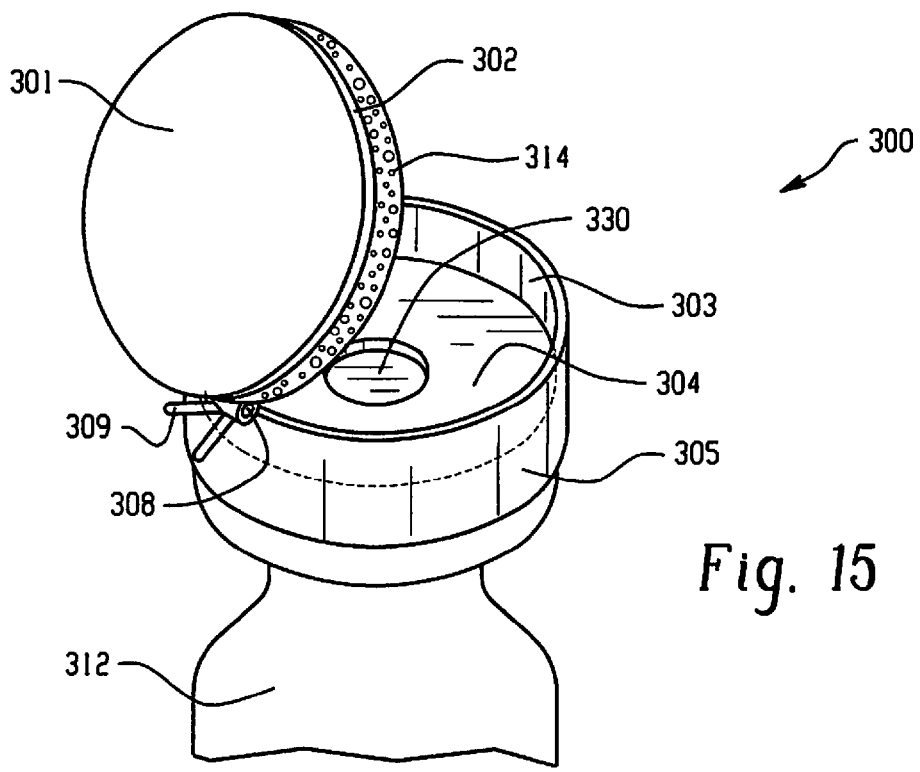
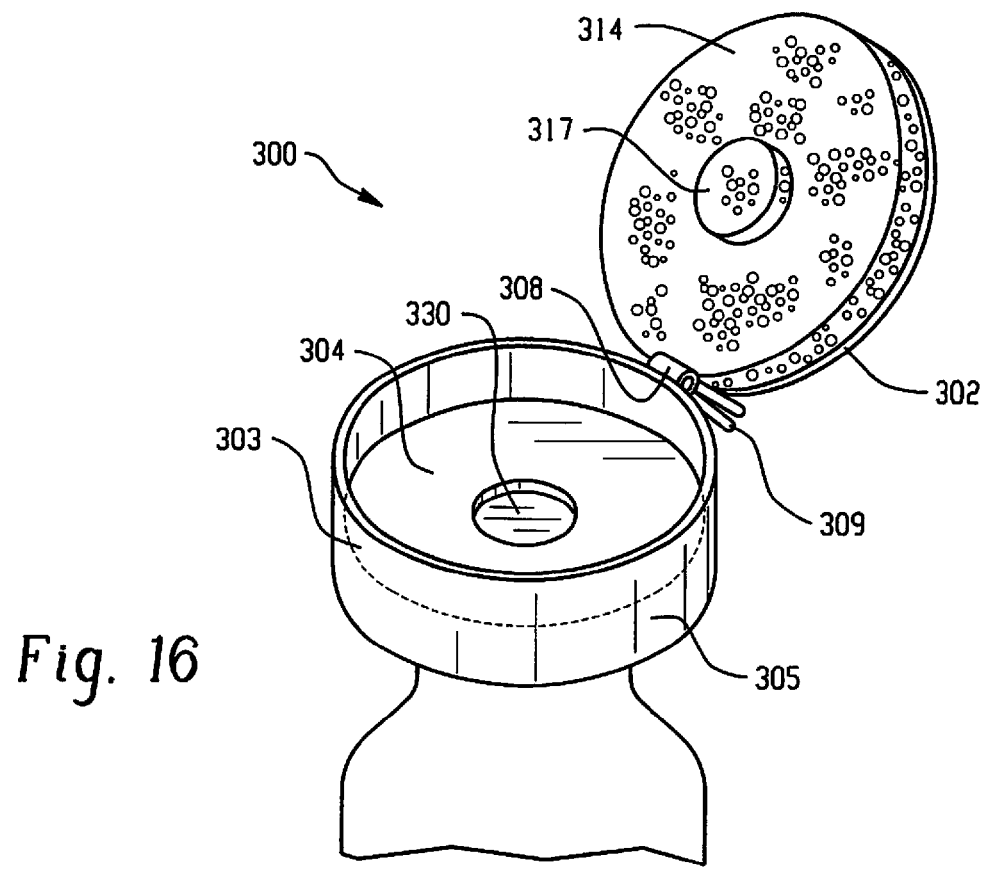

CAPPING DEVICE FOR DISINFECTING MEDICAL CONTAINER

BACKGROUND

The present invention generally relates to a self-disinfecting capping device, and more specifically, to a capping device for disinfecting a medical container.

Most medications for intravenous use are kept in either plastic or glass vials. After removing a protective plastic cap, a rubber membrane (also known as a septum) is penetrated with a sterile needle in order to draw medication into the syringe in an aseptic manner. In order to keep the rubber septum disinfected and prevent contamination of the vial, medical professionals ordinarily wipe the rubber septum with a pad containing a disinfecting agent. When faced with time constraints or stressful situations, only the most diligent specialists do so every time the medication is drawn. Medication vials can be made for a single or multiple uses. Sometimes during a surgery a medical provider has to repeatedly draw the medication from the same vial within an hour. Between these drawings, the vial having a punctured rubber septum may be exposed to various items containing blood or body fluids. This creates an opportunity for introduction of bloodstream infections if aseptic techniques are not strictly followed.

It is a custom for a medical professional to always use a new, sterile syringe and a new, sterile needle to access multi dose vials. However, even when they do so, it is still possible to introduce an infection if the rubber septum is contaminated. Occasionally, under pressure and stress, providers may utilize the same needle and the same syringe, which may be contaminated with blood or bacteria. In other situations, a needle may be left inside the rubber septum for future use. This practice causes vial contamination and may introduce bacteria into the bloodstream.

While it is not recommended to use the same needle and syringe to enter more than one medication vial because of the risks described above, there are circumstances where medication needs to be drawn more than once by the same syringe and needle (e.g., when reconstituting medications or vaccines).

Thus, there remains a need for a convenient and reliable disinfecting device that would allow medical professionals to carry out multiple drawings from the same container with 100% antiseptic techniques compliance.

SUMMARY

In an embodiment, a capping device for disinfection of a medical container is provided. The capping device includes a top portion having an inner surface, a bottom portion having an inner surface and an opening, and a connector. The connector couples the top portion of the capping device to the bottom portion thereof in a manner which permits movement of the top portion between a fully-seated position on the bottom portion of the capping device to form a hollow defined by the inner surface of the top portion of the capping device and the inner surface of the bottom portion thereof and a position apart from the opening to permit ingress to the vial. The capping device further includes a disinfecting absorbent material disposed inside the hollow and extending through the opening in the inner surface of the bottom portion. The capping device is configured for attachment to the medical container to bring the disinfecting absorbent material in contact with the medical container.

The top portion of the capping device may include a covering member and an upper sidewall disposed substantially perpendicular to and in contact with the covering member.

The bottom portion of the capping device may include a supporting member and a lower sidewall disposed substantially perpendicular to and in contact with the supporting member. The lower sidewall may extend through the inner surface of the supporting member to form an extension on the outer surface of the supporting member.

The bottom portion may further include an adhesive material disposed on the outer surface of the supporting member of the bottom portion, a side of the extension facing the outer surface of the supporting member of the bottom portion, or both.

The bottom portion may still further include a protecting member attached to the adhesive material.

The bottom portion may yet further include a sealing ring disposed within and in contact with the extension formed on the outer surface of the supporting member to provide a seal between the capping device and the medical container.

The opening may be substantially circular. It may be located approximately at the center of the supporting member of the bottom portion of the capping device.

The device further comprises a sealing member superimposed with and completely covering the opening.

The disinfecting absorbent material may be soaked with a disinfecting agent. It may be affixed to the inner surface of the top portion of the capping device.

In an embodiment, the connector may include a hinge which provides a pivotal connection between the upper sidewall of the top portion of the capping device and the lower sidewall of the bottom portion thereof. At least one handle may be attached to the hinge for application of an external force to move the top portion between the fully-seated position to the position apart from the opening.

In another embodiment, the connector may include a flexible material and the top portion may further include a handle for application of an external force to move the top portion between the fully-seated position to the position apart from the opening.

The connector may be adapted in such a way that, when the top portion is disposed at the position apart from the opening in the absence of an external force, the connector brings the top portion to the fully-seated position.

In another embodiment, a method for disinfecting a medical container is further provided. The method includes providing a capping device including a top portion having an inner surface, a bottom portion having an inner surface and an opening, and a connector. The connector couples the top portion of the capping device to the bottom portion thereof in a manner which permits movement of the top portion between a fully-seated position on the bottom portion of the capping device to form a hollow defined by the inner surface of the top portion of the capping device and the inner surface of the bottom portion thereof and a position apart from the opening to permit ingress to the vial. The capping device further includes a disinfecting absorbent material disposed inside the hollow and extending through the opening in the inner surface of the bottom portion. The method further includes attaching the capping device to the medical container to bring the disinfecting absorbent material in contact with the medical container.

The method may further include: applying an external force to the capping device to move the top portion thereof from the fully-seated position to the position apart from the opening.

The method may still further include: inserting a medical implement through the opening in the inner surface of the bottom portion of the capping device into the medical container to withdraw at least a portion of a content of the medical container and withdrawing the at least a portion of a content of the medical container into the medical implement.

The method may yet further include: moving the top portion of the capping device from the position apart from the opening to the fully-seated position to bring the disinfecting absorbent material in contact with the medical container.

BRIEF DESCRIPTION OF THE DRAWINGS

The above and other aspects and features of the present disclosure will become more apparent by describing in detail exemplary embodiments thereof with reference to the attached drawings, in which:

FIG. 15 is a perspective view of the capping device, according to another embodiment, wherein the top portion is not fully open; and FIG. 16 is a perspective view of the capping device, according to another embodiment, wherein the top portion is fully open.

DETAILED DESCRIPTION

Figure 1:
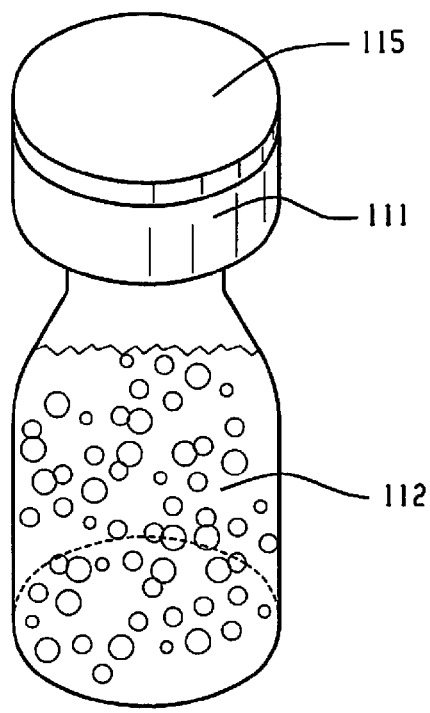
FIG. 1 is a view of a common medication vial before its first use.

Reference will now be made in detail to the embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The terms "substantially" and "approximately" as used herein are inclusive of the stated value and mean within an acceptable range of deviation for the particular value as determined by one of ordinary skill in the art, considering the measurement in question and the error associated with measurement of the particular quantity (i.e., the limitations of the measurement system). For example, "substantially" and "approximately" can mean within one or more standard deviations, or within ±30%, 20%, 10%, 5% of the stated value.

In an embodiment, a capping device for disinfection of a medical container is provided. The capping device includes a top portion having an inner surface, a bottom portion having an inner surface and an opening, and a connector. The connector couples the top portion of the capping device to the bottom portion thereof in a manner which permits movement of the top portion between a fully-seated position on the bottom portion of the capping device to form a hollow defined by the inner surface of the top portion of the capping device and the inner surface of the bottom portion thereof and a position apart from the opening to permit ingress to the vial. The capping device further includes a disinfecting absorbent material disposed inside the hollow and extending through the opening in the inner surface of the bottom portion. The capping device is configured for attachment to the medical container to bring the disinfecting absorbent material in contact with the medical container.

An embodiment of the present invention represents a new type of a cap with disinfecting properties for a medical container, for example, a vial. It guarantees full compliance with sterile techniques because after each use the top portion of the device with its disinfecting pad is biased toward its fully-seated (resting, closed) position at the top of the vial's rubber septum. Close contact between the disinfecting pad of the capping device and the rubber septum of the vial guarantees sterility of the septum at all times.

According to an embodiment, the capping device 100 includes a body which may be placed and affixed to the top of the medication vial (FIGS. 1-10). The body may be made of some light weight but rigid material, for example, thin plastic. The body of the device, according to an embodiment, is defined by a top portion (top cover) 101, an upper sidewall 102, a lower sidewall 103, and a supporting member (floor) 104. A connector (which may be a hinge) 108 may be disposed on the side of the device and may provide a pivotal connection between the upper sidewall 102 and the lower sidewall 103. Located inside the body is a disinfecting pad 114, which may be soaked with a disinfecting agent. The floor 104 has a central hole which corresponds in size and shape to the size and shape of a rubber septum 110 located on the top of the vial. The lower sidewall 103 extends down to form a slide on extension 105. The bottom surface of the floor 104 is covered with an adhesive material 106 which may be affixed to the top portion of a sealing ring 111 of the vial. The adhesive material 106 may also be used on the inside surface of the slide on extension 105 to affix to the side of the sealing ring 111, although the slide on extension 105 can just slip on and create a good connection with the side of the sealing ring 111. Two side handles (fins) 109 may be attached to the hinge.

A medical provider would press down on the upper fin and press up on the lower fin (to bring these two fins together), and this move would cause an upper part of the body to open and allow a needle to penetrate the rubber septum 110 and draw medication into the syringe (not shown). The hinge 108 may be biased to keep the upper part of the body of the capping device down and closed to assure that, after each use, the disinfecting pad 114 covers and sterilizes the rubber septum 110. Because of the presence of an opening (hole) in the floor of the capping device, the disinfecting pad 114 also has a pad extension 117 which corresponds in size and shape to the size and shape of the central hole as well as the rubber septum 110 beneath it. The disinfecting pad 114 may be affixed to the bottom surface of the top cover 101. At the bottom of the capping device is a peelable (removable) foil 107 which prevents drying of the adhesive material 106 and keeps the hollow part of the capping device sterile. The foil may be removed before the first use of the device. The capping device 100, according to an embodiment, would come in a sterile, sealed package, and the sterilization technique has to be carefully chosen without affecting the quality of the disinfecting agent.

FIG. 1 shows a common medication vial before its first use, when a plastic cap 115 is at the top of a sealing ring 111 and a rubber septum 110. The sealing ring 111 is usually made of a thin metal like aluminum. The rest of the vial is made of glass 112.

Figure 2:
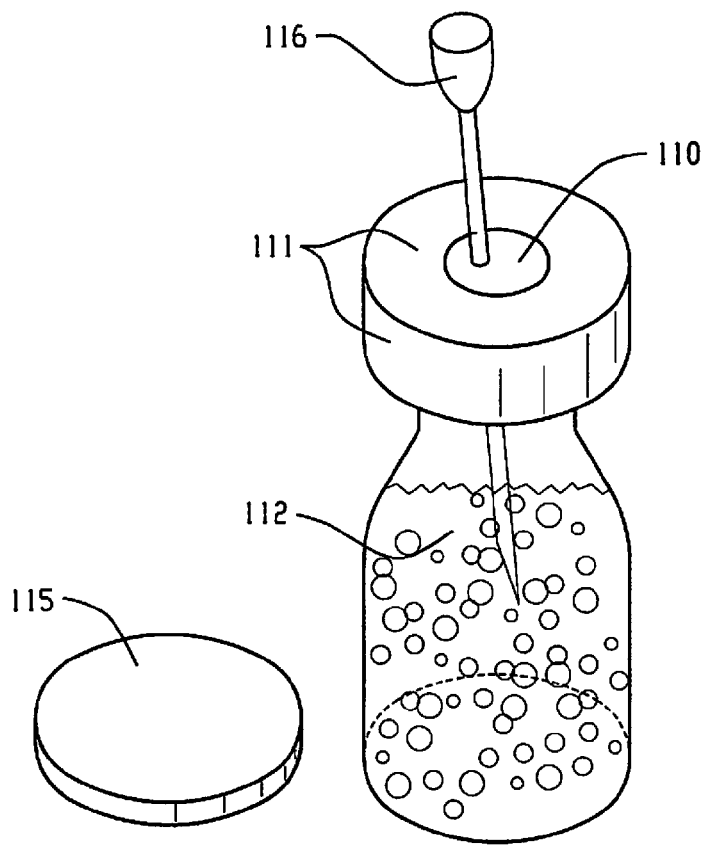
FIG. 2 is a view of the same common medication vial after the protective plastic cap is removed and the needle penetrated its rubber septum.

FIG. 2 provides a view of a common vial after the plastic cap 115 is removed. A needle 116 typically penetrates the rubber septum 110, which is usually made of a rubber material. The rest of the vial's top is covered with the sealing ring 111. Medication, most often in a liquid form, is found inside the glass 112 part of the vial.

Figure 3:
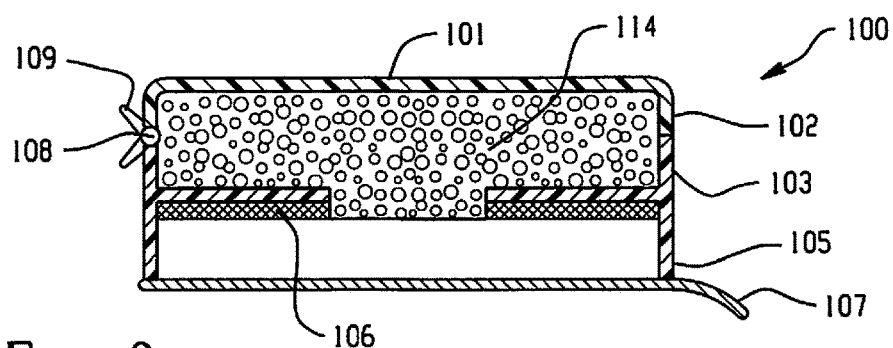
FIG. 3 is a cross-sectional view of the capping device, according to an embodiment, in a fully-seated position.

FIG. 3 illustrates a cross-sectional view of the capping device 100, according to an embodiment, before its first use. The body of the device is defined by the top cover 101, the upper sidewall 102, the lower sidewall 103, and the floor 104. The body may be made from a rigid but light material, such as plastic. Inside the device is the disinfecting pad 114 soaked with a disinfecting agent. The disinfecting pad 114 can be made from any suitable material having good absorbing ability, for example, a sponge. The lower sidewall 103 extends distally into the slide-on extension 105. Located at the bottom surface of the floor 104 is the adhesive material 106. In an embodiment, the adhesive material 106 may also be placed on the inner surface of the slide-on extensions 105. Located on the side of the capping device is the hinge 108 and attached to the hinge are two side fins 109. The hinge provides a pivotal connection between the upper 102 and lower 103 sidewalls. At the bottom of the device is a foil 107 which may be removed before the first use. The peelable foil 107 is designed to keep an area under the floor sterile. It also prevents drying of the adhesive material 106 at the bottom surface of the floor 104. The foil 107 may be made of various suitable materials known in the art.

Figure 4:
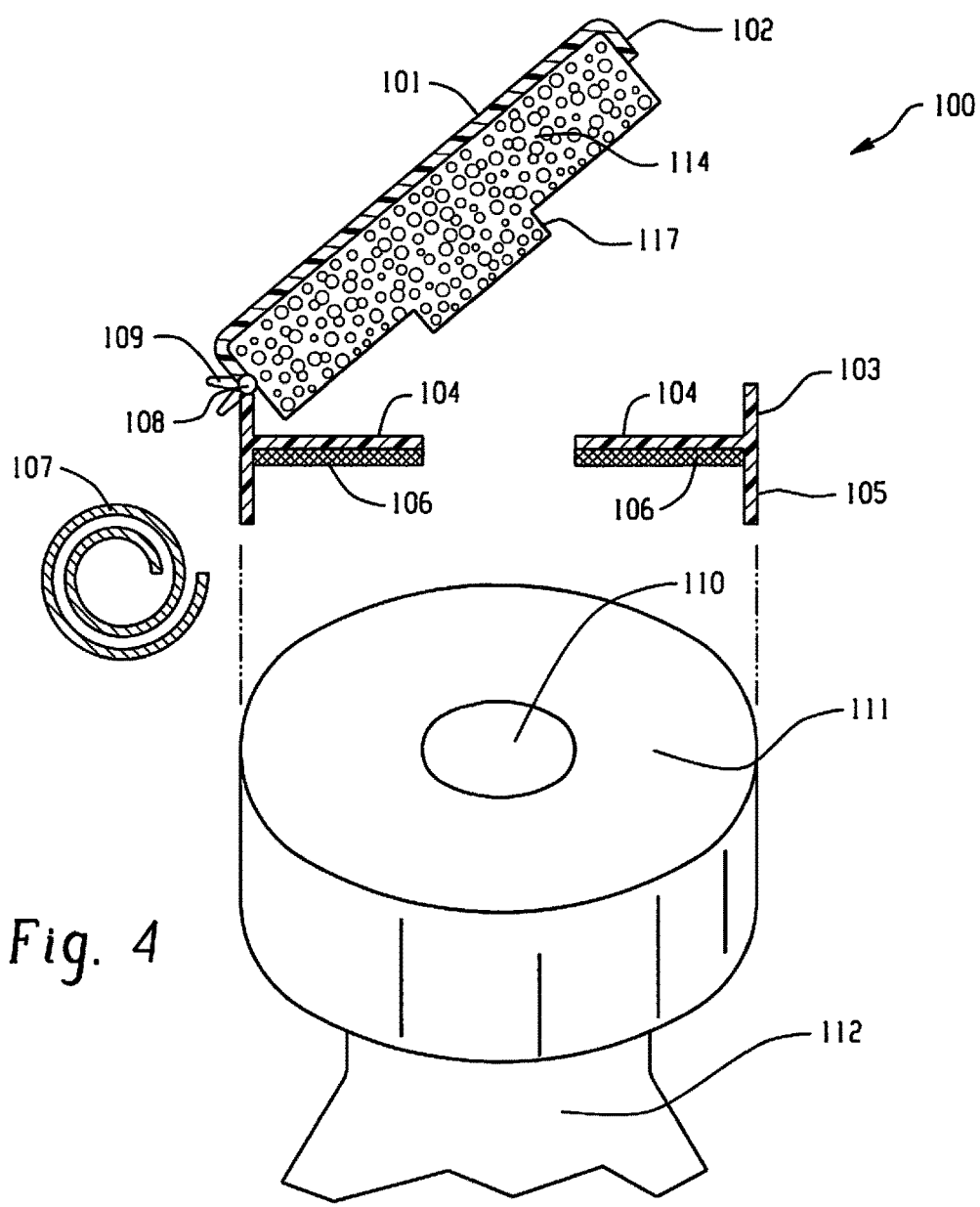
FIG. 4 is a cross-sectional view of the capping device, according to an embodiment, in a position apart from the opening showing a mode of attachment of the capping device to the medical container.

FIG. 4 illustrates the capping device with the top cover 101 partially open. The top cover 101 opens when a medical provider applies pressure on the side fins 109 and the hinge 108. In FIG. 4, the capping device is shown with the peelable foil 107 removed and ready to be placed at the top of a common medication vial. The slide on extensions 105 slide over the sidewalls of the sealing ring 111. The adhesive material 106 comes in contact with the top portion of the sealing ring 111 to form a bond. This bond plus tight contact between the slide on extension 105 and the sidewall of the sealing ring 111 would keep the device firmly affixed to the vial. The plastic floor 104 of the device has a central hole which corresponds in size to the size of the rubber septum 110 at the top of the vial. Thus, the central hole lacks both the plastic floor and the adhesive material. This central hole in the floor 104 is necessary for a needle to access the rubber septum 110 of the vial. The disinfecting pad 114 is affixed to the bottom surface of the top cover 101. The disinfecting pad 114 also has a central part extended (longer), and this pad extension 117 corresponds in shape and size to the central hole of the plastic floor 104 of the device and to the size of rubber septum 110 of the vial. A good size match is of critical importance since the pad extension 117 is a very important part of the device, according to an embodiment, which will keep the rubber septum 110 in contact with the disinfecting agent to keep it sterile at all times. The plastic floor 104 can be made from the same material as the top cover 101 and the sidewalls 102 and 103, or some other softer material, since the top of the vial will provide some extra support. The material may provide a fluid barrier to avoid leakage and loss of the disinfecting agent. Also, the upper 102 and lower 103 sidewalls may provide a good seal to prevent leakage and evaporation of the extra disinfecting agent which may be present in the body of the capping device. The amount of the disinfecting agent is usually small and the good absorbing ability of the disinfecting pad 114 should be enough to absorb it all.

Figure 5:
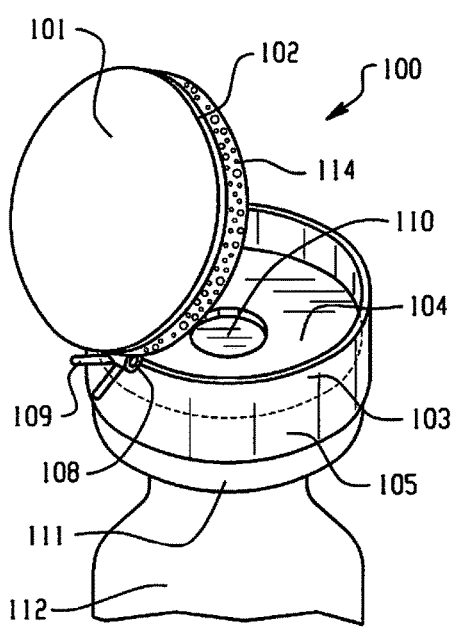
FIG. 5 is a perspective view of the capping device, according to an embodiment, in a position apart from the opening, wherein the capping device is attached to a medical container.
Figure 6:
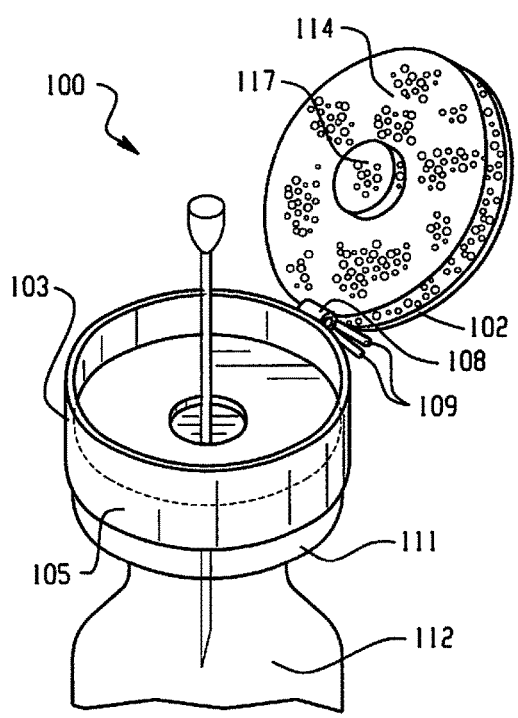
FIG. 6 is a perspective view of the capping device, according to an embodiment, in a position apart from the opening, wherein the capping device is attached to a medical container with a needle introduced through the opening into the medical container.

FIGS. 5-6 provide two perspective views of the capping device 100, according to an embodiment, from the top of a common vial at different angles. FIG. 5 displays the device in a partially opened view with the top cover 101 partially opened. This position is available when the side fins 109 are not pressed all the way down toward each other. The hinge 108 is biased to keep the top cover 101 closed and the disinfecting pad extension 117 in contact with the rubber septum 110. As long as the medical provider keeps pressure on the side fins 109, the top cover is open. When he or she releases the side fins 109, the top cover 101 closes. As a result, forced compliance with aseptic techniques is achieved and the rubber septum 110 is always kept sterile. In FIG. 5, the disinfecting pad 114 is partially shown, but the pad extension 117 cannot be seen. The slide on extension 115 is in close contact with the sidewall of the sealing ring 111. Most of the plastic floor 104 can be seen as well as its central hole with the rubber septum 110 beneath it. The upper 102 and lower 103 sidewalls of the body create a hollow (chamber) in which the disinfecting pad 114 is located. The dotted line represents the top edge of the sealing ring 111 and the border between the lower sidewall 103 and slide-on extension 105.

FIG. 6 shows the device fully opened and a needle 116 going through the central hole of the plastic floor 104 and through the rubber septum 110 sterilized by the pad 114 in order to draw medication from the vial. This figure allows a good view of the disinfecting pad 114 having the pad extension 117, the size and shape of which are the same as the size and shape of the central hole in the plastic floor 104. The disinfecting pad 114 is soaked with a disinfecting agent such as povidone iodine, alcohol, chlorhexidine, etc., or any combination of the disinfecting agents that provides antiseptic, antibacterial or antiviral properties. The disinfecting pad 114 can be made of a non-woven material or sponge from polyester, silicone, cotton, polyurethane, or any other absorbent material known in the art. The amount of the absorbent material may vary.

Figure 7:
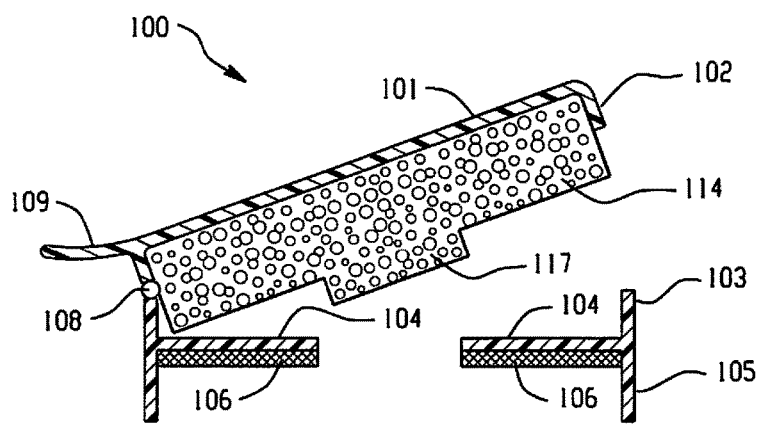
FIG. 7 is a cross-sectional view of the capping device, according to an embodiment, wherein a handle extends from the top cover.

FIG. 7 shows a cross-sectional view of the same capping device 100 but with only one side fin 109, which is a lateral protrusion (extension) of the top cover 101 at the same position as the hinge 108. The vial may be held in a hand, a provider may press the side fin 109 with his or her thumb, and the top cover 101 may open for medication withdrawal as a result. Release of the side fin 109 would cause the top cover 101 to close. The side fin 109 or protrusion may have some ridges on the top surface thereof to ensure a better grasp. The hinge 108 may keep the top cover 101 biased toward the closed position with the disinfecting pad in close contact with the rubber septum 110.

Figure 8:
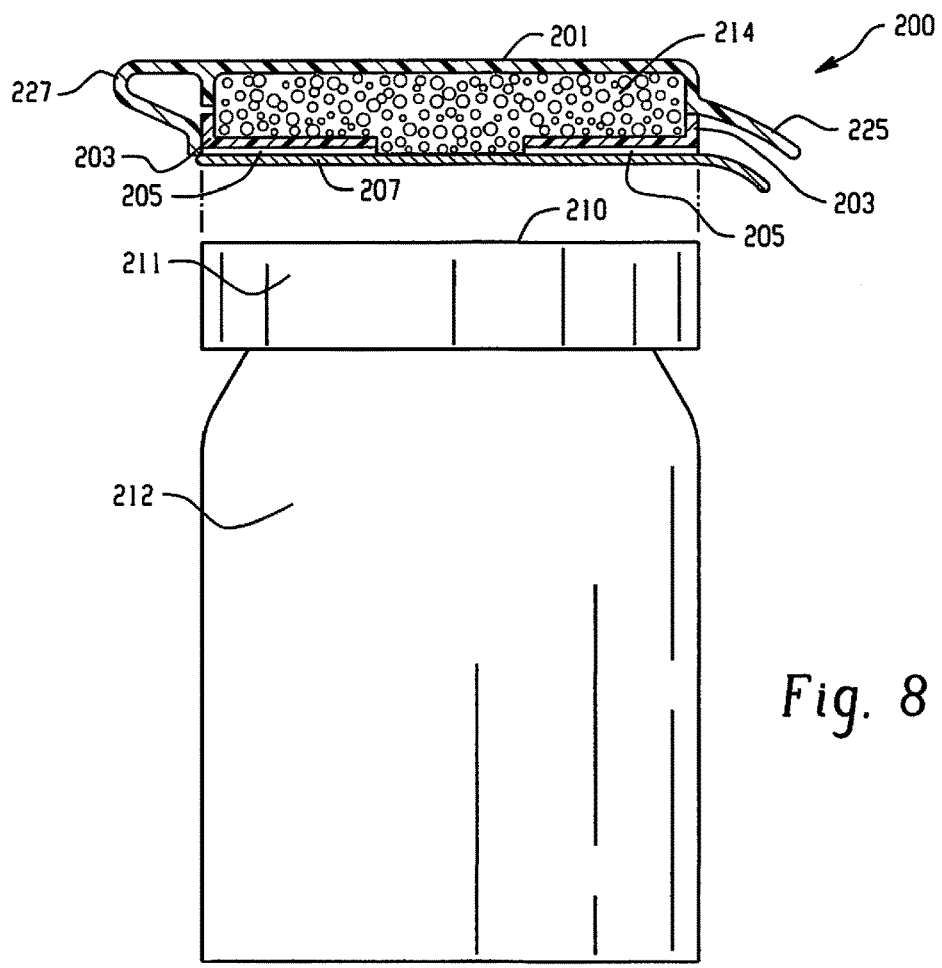
FIG. 8 is a cross-sectional view of the capping device, according to another embodiment, in a fully-seated position before its first use.
Figure 9:
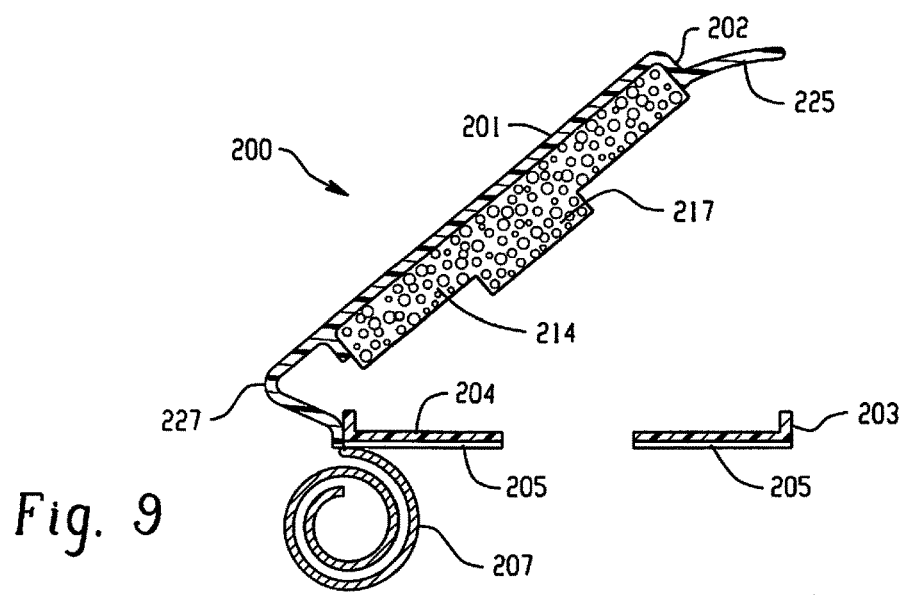
FIG. 9 is a cross-sectional view of the capping device, according to another embodiment, in a position apart from the opening with the peelable foil removed, wherein the capping device is ready to be placed at the top of common vial.

FIGS. 8-9 show another embodiment, which is a very simple and relatively inexpensive form of a capping device 200. It also contains a top cover 201, upper cover 202 and lower 203 sidewalls, and a floor 204. All these elements can be built from a foil or tape which is durable and which provides fluid barrier to prevent leakage and evaporation of the disinfecting agent. The capping device according to this embodiment also contains a bend 227 which keeps the upper 202 and lower 203 sidewalls together. The bend 227 may be made of a durable material to prevent its breakage. By keeping the parts together, the bend 227 is there to remind a medical provider to close the device after each use. The bend 227 is located opposite to the side extension 225 of the upper sidewall 202. The side extension 225 can have a different shape and size and may contain the adhesive material located at its bottom surface. When the device is in a fully-seated (rested, closed) position, the side extension 225 may be used to close the device by affixing to the lower sidewall 203 as well as to the side of the sealing ring 211. The capping device, according to this embodiment, does not have the slide on extension 105, or the hinge 108, but it still contains the peelable foil 207 as an embodiment described above.

FIG. 8 shows the capping device 200, according to an embodiment, in a closed (fully-seated) position, and FIG. 9 shows it in a position apart from the opening (open position). To open the device, a medical provider may lift the side extension up to separate it from the side of the sealing ring 211 and the lower sidewall 203. It is desirable that the adhesive material on the bottom surface of the side extension 225 would allow multiple taping and untaping (gluing and ungluing, removing and reaffixing). In FIG. 8, a common vial is shown with the rubber septum 210 and the sealing ring 211 to accept the capping device. In FIG. 9, the peelable foil 207 is shown almost completely removed. It is recommended that the side extension 225 also has its own peelable foil to protect the adhesive material before its first use. Also, the peelable foil 207 may be made longer on the side of the side extension 225 to cover its bottom surface too. The bottom surface of the floor 204 also contains the adhesive material 205. In this embodiment, the disinfecting pad 214 may be soaked with the disinfecting agent and can be seen with its central pad extension 217. In this embodiment, the disinfecting pad is usually thinner than in the embodiment above. The disinfecting pad 214 may be affixed to the bottom surface of the top cover 201 of the capping device 200. All elements may be thinner, simpler and lighter, compared to the embodiment above, because this embodiment is intended for a shorter time frame and fewer attempts to draw medication than the embodiment above.

Figure 10:
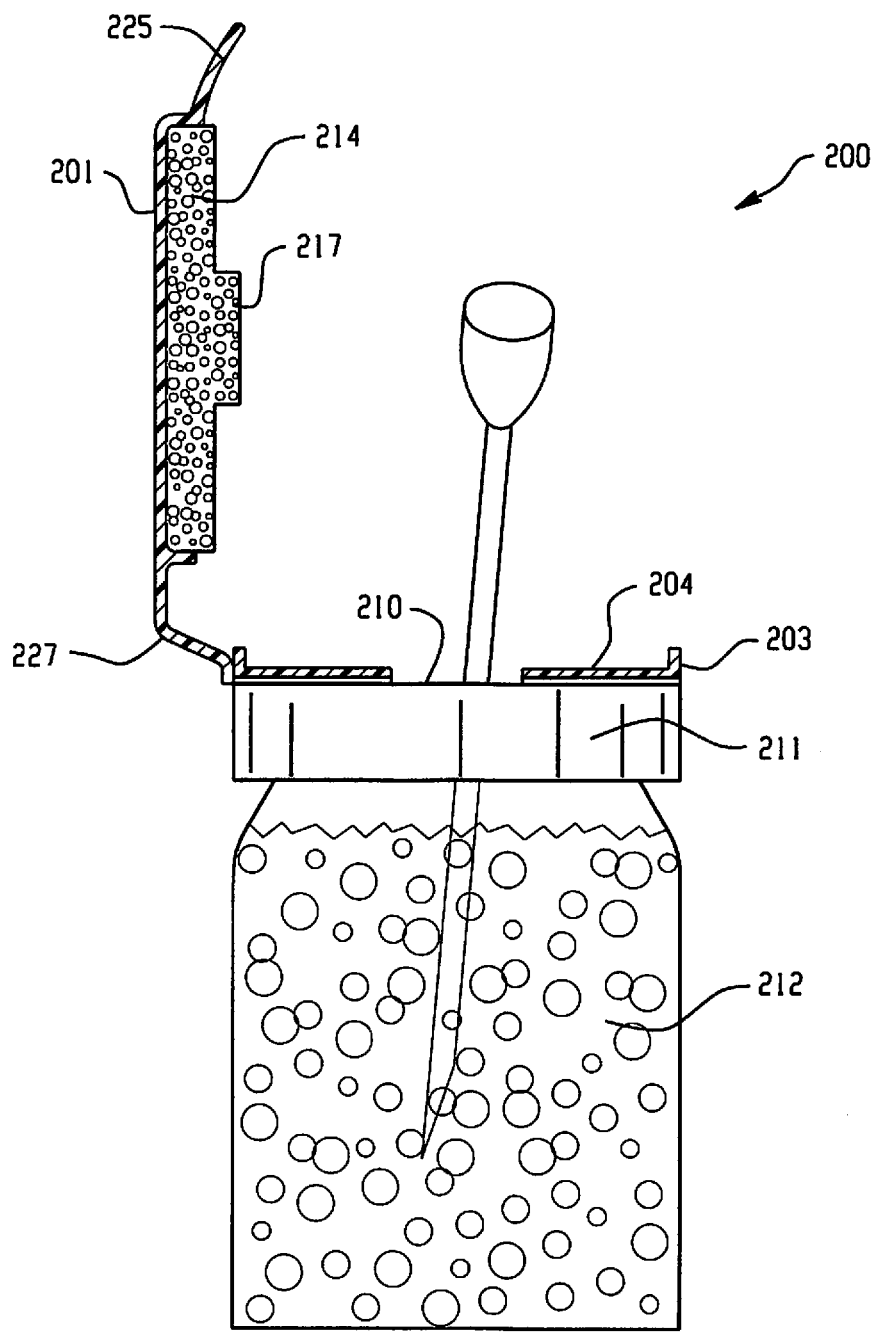
FIG. 10 is a cross-sectional view of the capping device, according to still another embodiment, wherein the capping device is placed on the top of a common medication vial, in a position apart from the opening, at the time when the needle is used to penetrate the rubber septum and draw the medication from the vial.

FIG. 10 shows the embodiment of the capping device 200 affixed to the top of the vial. To attach the device, the peelable foil 207 is removed first. The side extension 225 is lifted, the top portion of the invention including the disinfecting pad 214 is opened, and a needle is placed through the central hole of the floor 204 and through the rubber septum 210. The top portion of the device, which is shown only half-open although the bend 227, may be completely open, may hang from its attachment to the lower sidewall 203. The opened top cover 201 would remind the medical provider to return it into the fully-seated position after use and to keep the rubber septum 210 sterilized and ready for another use.

Figure 11:
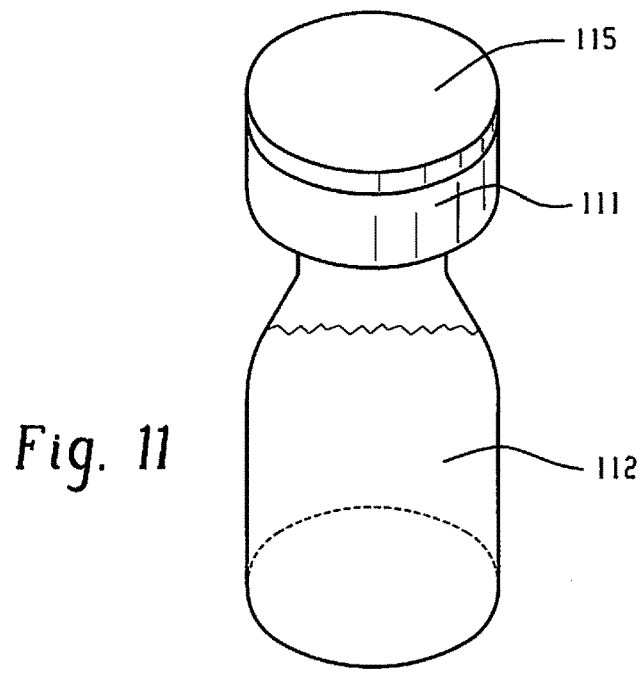
FIG. 11 is a view of a common medication vial having a protective cap before its first use.
Figure 12:
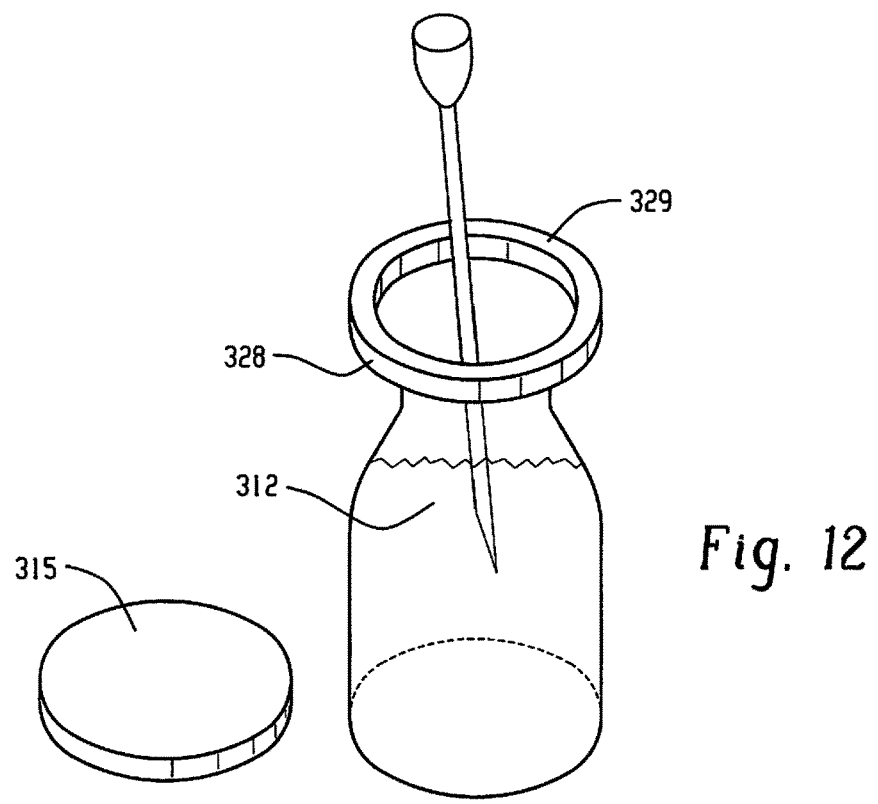
FIG. 12 is a view of the same medication vial after the protective cap, sealing ring, and rubber septum are removed, and after a needle is placed inside the vial through the top opening.

FIG. 11 shows a common medication vial before its first use. FIG. 12 shows the same vial after the protective cap, the sealing ring, and the rubber septum are removed and after a needle is placed inside the vial through the top opening.

Figure 13:
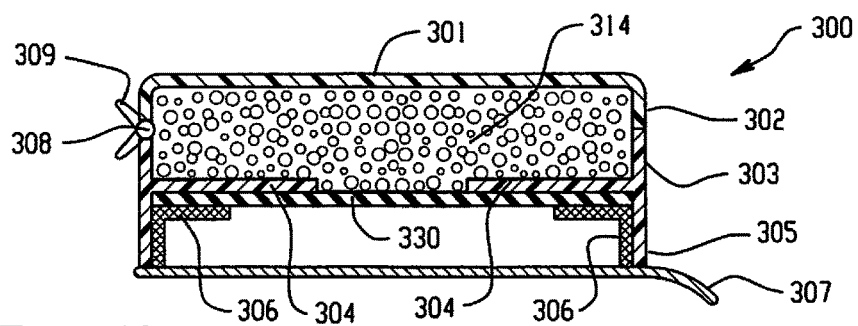
FIG. 13 is a cross-sectional view of the capping device, according to yet another embodiment, wherein the capping device is in a fully-seated position, before its first use.
Figure 14:
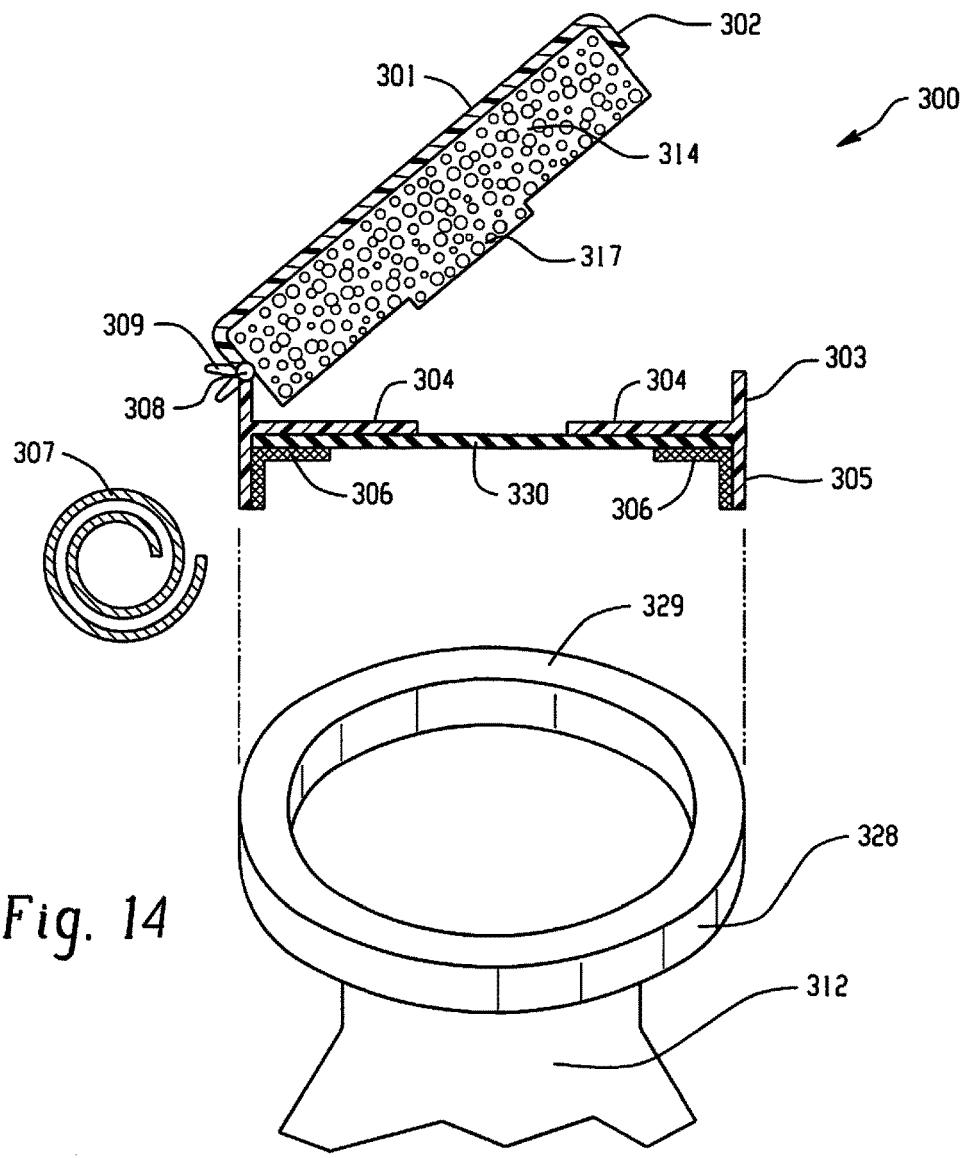
FIG. 14 is a cross-sectional view of the capping device, according to another embodiment, wherein the capping device is in a position apart from the opening and is ready for a needle to access the vial.

FIGS. 13-14 illustrate another embodiment of the capping device 300. It is similar to the initially described embodiment except for the addition of a rubber membrane 330 beneath the floor 304. The rubber membrane 330 may be desired for needle penetration and sterility, and is now a part of the capping device, according to an embodiment, and not a part of the vial. It should be noted that the rubber membrane 330 does not have a central hole like the floor 304. The rubber membrane 330 may potentially completely replace the floor 304 or may be added beneath the floor 304. In this embodiment, the adhesive material 306 is also present but only at the periphery of the device. It corresponds in size and shape to a top rim 329 of the vial 312 to which it affixes, having the plastic cap 315 taken off. It should also be noted that, in this embodiment, the adhesive material 306 is located at the bottom surface of the rubber membrane 330 and not on the floor 304 as in the embodiments described above. It is highly recommended that the adhesive material 306 is also present on the inside surface of the slide on extension 305 to assure good bonding between the sidewall of the vial 328 and the slide on extension 305. The two parts may snap on (when the diameters are complementary, so when the capping device is pushed down onto the top of the vial, the slide on extension 305 and the sidewall of the vial 328 would be in close contact, and would keep the two parts together, the slide on extension 305 to slip-fit over sidewall of the vial 328).

FIGS. 15-16 show two perspective views from different angles of the capping device 300, according to this embodiment, at the top of a common vial. As previously mentioned, some medication vials are different and need not only the cap 315, but also the sealing ring 311 and rubber septum 310 to be removed before use. In FIG. 15, the capping device 300 is shown in a partially opened view with the top cover 301 partially opened. This happens when the side fins 309 are not pressed all the way down toward each other. The hinge 308 is biased to keep the top cover 301 closed and the disinfecting pad extension 317 from touching the rubber membrane 330. As long as a medical provider keeps pressure on the side fins 309, the top cover is open. When he or she releases the side fins 309, the top cover 301 closes. As a result, forced compliance with aseptic techniques is achieved, and the rubber membrane 330 is always kept sterile. In this view, the disinfecting pad 314 is partially shown, but the pad extension 317 cannot be seen. The disinfecting pad 314 is affixed to the bottom surface of the top cover 301. The slide on extension 305 is in close contact with the sidewall of the vial 328. Most of the floor 304 can be seen as well as its central hole with the rubber membrane 303 underneath. The upper 302 and lower 303 sidewalls of the body create a chamber in which the disinfecting 314 pad is located. The dotted line represents the top edge of the vial's sidewall 328 and the border between the lower sidewall 303 and the slide-on extension 305.

FIG. 16 shows the capping device 300, according to the embodiment, fully opened and ready for a needle to penetrate through the central hole of the floor 304 and through the rubber membrane 330 sterilized by the pad 314 in order to draw medication from the vial. This figure allows a good view of the disinfecting pad 314 with its pad extension 317, the size and shape of which are the same as the size and shape of the central hole in the floor 304. The disinfecting pad 314 is soaked with a disinfecting agent such as povidone iodine, alcohol, chlorhexidine, etc., or any combination of the disinfecting agents that provides antiseptic, antibacterial or antiviral properties. The disinfecting pad 314 can be made of a non-woven material or sponge from polyester, silicone, cotton, polyurethane, or any other absorbent material known in the art. The amount of the absorbent material may vary.

All embodiments of the invention described above may be used not only on medication vials but also on any type of vials, jars, boxes, packages, buckets, etc., penetrated with sharp objects, where sterility and cleanness is required.

In another embodiment, a method for disinfecting a medical container is further provided. The method includes providing a capping device including a top portion having an inner surface, a bottom portion having an inner surface and an opening, and a connector. The connector couples the top portion of the capping device to the bottom portion thereof in a manner which permits movement of the top portion between a fully-seated position on the bottom portion of the capping device to form a hollow defined by the inner surface of the top portion of the capping device and the inner surface of the bottom portion thereof, and a position apart from the opening to permit ingress to the vial. The capping device further includes a disinfecting absorbent material disposed inside the hollow and extending through the opening in the inner surface of the bottom portion. The method further includes attaching the capping device to the medical container to bring the disinfecting absorbent material in contact with the medical container.

The method may further include: applying an external force to the capping device to move the top portion thereof from the fully-seated position to the position apart from the opening.

The method may still further include: inserting a medical implement through the opening in the inner surface of the bottom portion of the capping device into the medical container to withdraw at least a portion of a content of the medical container and withdrawing the at least a portion of a content of the medical container into the medical implement.

The method may yet further include: moving the top portion of the capping device from the position apart from the opening to the fully-seated position to bring the disinfecting absorbent material in contact with the medical container.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A capping device for disinfection of a medical container, comprising:
   a top portion comprising an inner surface;
   a bottom portion comprising an inner surface and an opening;

a connector coupling the top portion of the capping device to the bottom portion thereof in a manner which permits movement of the top portion between
- a fully-seated position on the bottom portion of the capping device to form a hollow defined by the inner surface of the top portion of the capping device and the inner surface of the bottom portion thereof, and
- a position apart from the opening to permit ingress to the vial, and a disinfecting absorbent material disposed inside the hollow and extending through the opening in the inner surface of the bottom portion, wherein the capping device is configured for attachment to the medical container to bring the disinfecting absorbent material in contact with the medical container.

2. The capping device according to claim 1, wherein the top portion comprises a covering member and an upper sidewall disposed substantially perpendicular to and in contact with the covering member.

3. The capping device according to claim 1, wherein the bottom portion comprises a supporting member and a lower sidewall disposed substantially perpendicular to and in contact with the supporting member.

4. The capping device according to claim 3, wherein the opening is located approximately at the center of the supporting member of the bottom portion of the capping device.

5. The capping device according to claim 3, wherein the opening is substantially circular.

6. The capping device according to claim 1, wherein the disinfecting absorbent material is affixed to the inner surface of the top portion of the capping device.

7. The capping device according to claim 1, wherein the disinfecting absorbent material is soaked with a disinfecting agent.

8. The capping device according to claim 3, wherein the lower sidewall extends through the inner surface of the supporting member to form an extension on the outer surface of the supporting member.

9. The capping device according to claim 1, wherein the connector comprises
- a hinge providing a pivotal connection between the upper sidewall of the top portion of the capping device and the lower sidewall of the bottom portion thereof, and
- at least one handle attached to the hinge for application of an external force to move the top portion between the fully-seated position to the position apart from the opening.

10. The capping device according to claim 8, wherein the bottom portion further comprises an adhesive material disposed on the outer surface of the supporting member of the bottom portion, a side of the extension facing the outer surface of the supporting member of the bottom portion, or both.

11. The capping device according to claim 10, wherein the bottom portion further comprises a protecting member attached to the adhesive material.

12. The capping device according to claim 10, wherein the bottom portion further comprises a sealing ring disposed within and in contact with the extension formed on the outer surface of the supporting member to provide a seal between the capping device and the medical container.

13. The capping device according to claim 1, wherein the device further comprises a sealing member superimposed with and completely covering the opening.

14. The capping device according to claim 1, wherein the connector is adapted such that, when the top portion is disposed at the position apart from the opening in the absence of an external force, the connector brings the top portion to the fully-seated position.

15. The capping device of claim 1,
wherein the connector comprises a flexible material, and
wherein the top portion further comprises a handle for application of an external force to move the top portion between the fully-seated position to the position apart from the opening.

16. A method for disinfecting a medical container, comprising:
providing a capping device comprising:
- a top portion comprising an inner surface;
- a bottom portion comprising an inner surface and an opening;
- a connector coupling the top portion of the capping device to the bottom portion thereof in a manner which permits movement of the top portion between
  - a fully-seated position on the bottom portion of the capping device to form a hollow defined by the inner surface of the top portion of the capping device and the inner surface of the bottom portion thereof, and
  - a position apart from the opening to permit ingress to the vial, and
- a disinfecting absorbent material disposed inside the hollow and extending through the opening in the inner surface of the bottom portion, wherein the capping device is configured for attachment to the medical container, and attaching the capping device to the medical container to bring the disinfecting absorbent material in contact with the medical container.

17. The method according to claim 16, further comprising applying an external force to the capping device to move the top portion thereof from the fully-seated position to the position apart from the opening.

18. The method according to claim 17, further comprising inserting a medical implement through the opening in the inner surface of the bottom portion of the capping device into the medical container to withdraw at least a portion of a content of the medical container.

19. The method according to claim 18, further comprising withdrawing the at least a portion of a content of the medical container into the medical implement.

20. The method according to claim 19, further comprising moving the top portion of the capping device from the position apart from the opening to the fully-seated position to bring the disinfecting absorbent material in contact with the medical container.

* * * * *